United States Patent [19]

Kurtz et al.

[11] 4,111,983
[45] Sep. 5, 1978

[54] OXIDATION OF UNSATURATED ALDEHYDES TO UNSATURATED ACIDS

[75] Inventors: Abraham N. Kurtz, Charleston; Robert W. Cunningham, Saint Albans, both of W. Va.; Alfred W. Naumann, Monsey, N.Y.

[73] Assignee: Union Carbide Corporation, New York, N.Y.

[21] Appl. No.: 407,577

[22] Filed: Oct. 18, 1973

[51] Int. Cl.$^2$ .............................................. C07C 51/32
[52] U.S. Cl. ........................ 562/535; 252/455 R; 252/456; 252/464; 252/467; 260/413
[58] Field of Search ........................... 260/530 N, 413; 252/467, 456, 464, 455 R

[56] References Cited

U.S. PATENT DOCUMENTS

| | | | |
|---|---|---|---|
| 3,736,355 | 3/1973 | Croci et al. | 260/533 N |
| 3,761,516 | 9/1973 | Khoobiar | 260/530 N |
| 3,775,474 | 11/1973 | Ohara et al. | 260/530 N |
| 3,833,649 | 9/1974 | Wada | 260/530 X |
| 3,867,345 | 2/1975 | Koberstein | 260/530 X |

*Primary Examiner*—Vivian Garner
*Attorney, Agent, or Firm*—Donald M. Papuga

[57] ABSTRACT

An improved process for catalytically oxidizing alpha-beta unsaturated aliphatic aldehydes in the vapor phase with molecular oxygen to produce alpha-beta unsaturated carboxylic acids using a catalyst composition which has been thermally activated in the presence of ammonia, and which comprises the elements Mo, V, W, Cr and Cu.

10 Claims, No Drawings

OXIDATION OF UNSATURATED ALDEHYDES TO UNSATURATED ACIDS

BACKGROUND OF THE INVENTION

1. Field of the Invention

The invention relates to the vapor phase catalytic oxidation of unsaturated aliphatic aldehydes to the corresponding unsaturated carboxylic acid.

2. Description of the Prior Art

Belgian Pat. No. 774,329 and Netherlands Patent Application No. 72-05595 disclose the use of a catalyst containing the elements Mo, V, W, Cr, and Cu, in various atom-mole ratios thereof, for the vapor phase catalytic oxidation of acrolein to acrylic acid. These publications indicate that the catalysts are prepared by a thermal treatment of a mixture of compounds of the elements Mo, V, W, Cr and Cu.

The terms % conversion, productivity and % selectivity which are employed herein with respect to the present invention are defined as follows:

$$\% \text{ conversion} = 100 \times \frac{A}{\text{moles of aldehyde in the reaction mixture which is fed to the catalyst bed per hour of reaction time}} \quad \text{I}$$

wherein $A =$ the molar aldehyde-equivalent sum (carbon basis) of all carbon-containing products, excluding the aldehyde in the effluent, which are produced per hour of reaction time  Ia productivity = pounds of alpha-beta unsaturated aliphatic carboxylic acid product produced per cubic foot of catalyst (in the catalyst bed) per hour of reaction time  II $$\% \text{ selectivity (or efficiency)} = 100 \times \frac{\text{moles of alpha-beta unsaturated aliphatic carboxylic acid produced per hour of reaction time}}{A} \quad \text{III}$$

wherein A is as defined above in equation Ia.

SUMMARY OF THE INVENTION

Alpha-beta unsaturated aliphatic carboxylic acids are produced with a relatively high % conversion, productivity and % selectivity by oxidizing the corresponding alpha-beta unsaturated aldehyde in the vapor phase by contacting the aldehyde, in the presence of molecular oxygen and steam, with a catalyst composition comprising the elements Mo, V, W, Cr, and Cu, which have been thermally activated in the presence of ammonia.

An object of the present invention is to provide novel catalyst compositions for the vapor phase oxidation of alpha-beta unsaturated aliphatic aldehydes to the corresponding alpha-beta unsaturated aliphatic carboxylic acid.

A further object of the present invention is to provide a process whereby alpha-beta unsaturated aliphatic aldehydes can be oxidized in the gas phase so as to produce the corresponding alpha-beta unsaturated aliphatic carboxylic acid with a relatively high level of % conversion, productivity and % selectivity.

These and other objects of the present invention are achieved by using as such a catalyst in such a process a composition which has been thermally activated in the presence of ammonia and which contains the elements Mo, V, W, Cr and Cu in the following atomic ratio relationship:

$$Mo_a V_b W_c Cr_d Cu_e$$

wherein
$a$ is 12
$b$ is 1 to 6, and preferably 4 to 5,
$c$ is 1 to 6, and preferably 2 to 3,
$d$ is 0 to 2, and preferably 0.5 to 1, and
$e$ is 1 to 4, and preferably 2 to 3.

The numerical values of $a, b, c, d$ and $e$ represent the relative atom mole ratios of the elements Mo, V, W, Cr and Cu, respectively, which are present in the catalyst composition.

The Catalyst

The elements Mo, V, W, Cr and Cu are present in the catalyst composition in combination with oxygen, in the form, it is believed, of various metal oxides, so as to provide a composition which, where subjected to X-ray diffraction, is characterized by a relatively well developed reflection corresponding to a lattice spacing of approximately 4A and a cluster of weaker peaks in the 3 to 4A interval.

The catalyst is preferably prepared from an aqueous solution of mutually water soluble salts or compounds of each of the metals Mo, V, W, Cr and Cu. The selected salts, complexes or compounds should be mutually soluble in water having a pH of 1–12, and preferably 5 ± 3, at a temperature of about 20° to 100° C. The solution of the metal containing compounds is prepared by dissolving sufficient quantities of soluble compounds of each of the metals so as to provide the desired $a:b:c:d:e$ atom mole ratios of the elements Mo, V, W, Cr and Cu, respectively. The catalyst composition is then prepared by separating the water or the resulting mixture of the metal compounds from the solution system. The water can be removed by evaporation.

It has been found that the more active catalysts are prepared more readily if they are prepared from relatively dilute solutions thereof. For this reason it is preferred, in preparing such solutions that at least 6, and preferably at least 8, liters of water (at 25° C) are used in dissolving about every 1250 grams of the soluble compounds. Lesser amounts of water can be used, although the resulting catalysts may not be as active.

Where the catalyst is to be used on a support, the metal compounds are deposited on a porous support having a surface area of about 0.01 to 2 square meters per gram. The support has an apparent porosity of 30–60%; at least 90% of the pores have a pore diameter in the range of 20–1500 microns. The support is usually used in the form of particles or pellets which are about ⅛ to 5/16 inch in diameter. The deposition is preferably accomplished by immersing the support in the solution after a major portion of the solvent has been evaporated from the solution and then evaporating the major portion of the solvent and then drying the system at about 80° to 140° C. for 2 to 60 hours. The thus dried catalyst is then activated by being thermally treated by being heated at about 350° to < 450° C, and preferably at 400° ± 25° C. for about 2 to 24 hours in an atmosphere of air and/or nitrogen containing about 0.1 to 1% by volume of ammonia to produce the $Mo_a V_b W_c Cr_d Cu_e$ composition. Prior to the actual thermal activation of the dried catalyst at > 350° C., the catalyst is heated up to the activation temperatures over a period of about 0.5 to 3 hours in order to allow for heat losses and gains that might arise in the catalyst composition as a result of endothermic and/or exothermic reactions that may occur during this preheating operation. The heating can be conducted by indirect heat exchange means so as to avoid removal of the ammonia containing atmosphere during the thermal treatment of the catalyst.

The support materials which may be used include silica and alumina, and other inert support materials and mixtures thereof. The supported catalyst may be used as a fixed or fluidized bed.

When used on the support, the supported oxides usually comprise about 10 to 50 weight % of the total catalyst composition; of the total catalyst composition about 50 to 90 weight % is support.

The molybdenum is preferably introduced into solution in the form of ammonium salts thereof such as ammonium paramolybdate and organic acid salts of molybdenum such as acetates, oxalates, mandelates and glycolates. Other water soluble molybdenum compounds which may be used are partially water soluble molybdenum oxides, molybdic acid and the nitrates and chlorides of molybdenum.

The vanadium is preferably introduced into solution in the form of ammonium salts thereof such as ammonium metavanadate and ammonium decavanadate, and organic acid salts of vanadium such as acetates, oxalates and tartrates. Other water soluble vanadium compounds which may be used are partially water soluble vanadium oxides, and the sulfates and nitrates of vanadium.

The tungsten is preferably introduced into solution in the form of ammonium salts such as ammonium paratungstate. Other water soluble tungsten compounds which may be used are the tungstic acids.

The copper and chromium are preferably introduced into solution in the form of nitrates. Other water soluble compounds of these elements which may be used are the water soluble acetates, lactates, salicylates and formates of such metals, and ammonium dichromate.

The Aldehydes

The alpha-beta unsaturated aldehydes which are oxidized in the process of the present invention have the structure

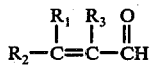

wherein $R_1$ is H or a $C_1$ - $C_6$ alkyl radical, and $R_2$ and $R_3$ are the same or different and are H or $CH_3$.

These aldehydes thus include acrolein and methacrolein. Where acrolein and/or methacrolein are oxidized, the corresponding alpha-beta unsaturated carboxylic acid would be acrylic acid and/or methacrylic acid, respectively.

The aldehydes may be oxidized individually or in combinations thereof.

The Reaction Mixture

The components of the reaction mixtures which are employed in the process of the present invention, and the relative ratios of the components in such mixtures, are the following:
1 mole of aldehyde,
0.2 to 5 moles of molecular oxygen (as pure oxygen or in the form of air),
1 to 25 moles of water (in the form of steam),
and, optionally, 0.1 to 5 moles of alpha-beta unsaturated olefin having the same number of carbon atoms as the aldehyde(s) being oxidized. Propylene, for example, can be used in the reaction mixture when acrolein is being oxidized to acrylic acid.

The water or steam is used as a reaction diluent and as a heat moderator for the reaction. Other diluents which may be used are inert gases, such as nitrogen, $CO_2$ and gaseous saturated hydrocarbons.

The olefin may be present due to the fact that the aldehyde feed may be emanating as the effluent from an olefin → aldehyde oxidation reaction process, and such effluent usually contains unreacted olefin.

The components of the reaction mixture are uniformly admixed prior to being introduced into the reaction zone. The components are preheated, individually or after being admixed, prior to their being introduced into the reaction zone, to a temperature of about 200° to 300° C.

Reaction Conditions

The preheated reaction mixture is brought into contact with the catalyst composition, in the reaction zone, under the following conditions:
pressure of about 1 to 10, and preferably of about 1 to 3 atmospheres,
temperature of about 200° to 400° C., and preferably of about 275° to 375° C.
contact time (reaction mixture on catalyst) of about 0.1 to 10, and preferably of about 1 to 3 seconds, and at a space velocity of about 1000 to 6000 $h^{-1}$, preferably 4000 to 5000 $h^{-1}$.

The contact time may also be defined as the ratio between the apparent volume of the catalyst bed and the volume of the gaseous reaction mixture fed to the catalyst bed under the given reaction conditions in a unit of time.

The reaction pressure is initially provided by the feed of gaseous reactants and diluents, and after the reaction is commenced, the pressure is maintained, preferably, by the use of suitable back-pressure controllers placed on the gaseous effluent side of the catalyst bed.

The reaction temperature is preferably provided by placing the catalyst bed within a tubular converter whose walls are immersed in a suitable heat transfer medium, such as tetralin, or molten salt mixtures, which is heated to the desired reaction temperature.

The following examples are merely illustrative of the present invention and are not intended as a limitation upon the scope thereof.

The examples provided below disclose the preparation of various catalyst compositions and the use of such compositions in the oxidation of acrolein to acrylic acid.

The activity of each experimental catalyst was determined in a jacketed one-inch stainless steel reactor or converter tube 78 inches long. The jacket contained tetralin which served as a heat transfer medium.

The center portion (55 inches) of the reactor tube was charged with 800 ml of catalyst with a one-eighth inch movable thermocouple in the catalyst bed.

The catalysts were treated at 30 psig, with a space velocity of 4600 $hr^{-1}$ or contact time of 1.2 seconds, and an inlet feed composed of 3 mole % acrolein, 6 mole % oxygen, 15 mole % steam, and 76 mole % nitrogen.

The activity of the catalysts was tested by adjusting the temperature of the reactor tube jacket to produce a maximum temperature (hot spot) of 304°-306° C. in the catalyst bed while the oxidation reaction was occurring.

Space velocity is calculated by determining the total reactor outlet gas equivalents (liters) of the total effluent evolved over a period of one hour. This room temperature volume is converted to the volume at 0° C. at 760 mm Hg.

$$\text{Space Velocity} = \frac{\text{liters of outlet gas equivalents/hour}}{\text{liters of catalyst in reactor}} \quad \text{IV}$$

$$= \frac{1}{\text{hours at } °\text{C and atmospheric pressure}}$$

EXAMPLE 1

(Describes preparation of catalyst up to the thermal activation step)

Cupric nitrate trihydrate in the amount of 172 grams (0.712 gm atoms copper) was dissolved in 1600 cc water at 70° C. and the solution placed in a 12 inch diam. × 6 inch deep stainless steel evaporating dish resting in a steam bath. To this solution in rapid succession there were added 676 grams ammonium paramolybdate (3.828 gram-atoms molybdenum), 24 grams ammonium dichromate (0.1904 gram atoms chromium), 200 grams ammonium paratungstate $[(NH_4)_{10}W_{12}O_{41}.5H_2O]$ (0.772 gram atoms tungsten), and 172 grams ammonium metavanadate (1.47 gram atoms vanadium) with good mixing and stirring. While continuing the mixing the temperature was raised to concentrate the system by evaporation. After 3–3.5 hours an additional quantity of 200 cc. water was added in three increments to maintain the resultant slurry at a desirable degree of thinness prior to addition of the support. At this point two liters of ¼-inch spheres of Norton SA5218 catalyst support (2080 gram) was added to the slurry and the whole mixed thoroughly while evaporating to dryness for a period of 140 minutes.

EXAMPLE 2

(describes thermal activation by direct heat exchange)

The catalyst prepared according to Example 1 was charged to a container basket consisting of a stainless steel cylinder 6 inches in diameter × 11½ inches in length equipped with an eight mesh wire bottom on which the catalyst bed rested. The basket was then placed within an insulated tight-fitting cylinder such that when air was blown into the bottom of the resulting array the air of necessity would be forced to pass through the bed of catalyst granules. The thermal activation was then carried out by passing pre-heated air through the above-described catalyst bed in the amount of 16000 liters per hour. Over a period of 45 minutes the air temperature was raised to 200° C., then over a period of 60 minutes the air temperature was raised to 300° C., then over a period of 60 minutes the air temperature was raised to 400° C., after which the air was held at 400° C. for a period of 5 hours. Thermocouples placed at the middle and the top of the catalyst bed showed close correspondence to the incoming air temperatures. No more visible fumes (steam, ammonia, etc.) were observed to emanate from the gas outlet side of the catalyst bed once the catalyst bed reached temperatures of 338°–343° C. A 78.8% of theoretical yield of deposited oxides was achieved, with an estimated 26.2% active oxide content, assuming for purposes of calculation that the elements existed as $MoO_3$, $V_2O_5$, $WO_3$, $CuO$, and $Cr_2O_3$. (The losses were largely due to the incomplete retention of active ingredients by the support during the initial impregnation operations.) The surface area amounted to 1.4 $m^2$/gram. The resulting catalyst was tested in the manner described above for the standard acrolein oxidation test. At a jacket temperature of 286° C. and a catalyst temperature (maximum) of 305° C. acrolein was converted to the extent of 40.8%, productivity amounted to 9.4 lbs. acrylic acid per cubic foot catalyst per hour and selectivity amounted to 77.9%.

EXAMPLE 3

(Describes effect of excluding oxygen)

Catalyst was prepared in a manner described in Example 1. Thermal activation was carried out as described in Example 2, however, 16000 liters per hour of nitrogen was used in place of air and only one liter of catalyst was charged to the basket. In the heating cycle, over a period of 60 minutes the temperature of the nitrogen was raised to 200° C, then over a period of 30 minutes the temperature of the nitrogen was raised to 300° C, then over a period of 30 minutes the temperature of the nitrogen was raised to 400° C, after which the temperature of the nitrogen was held at 400° C for a period of 5 hours. The yield of catalyst was 82.2% of theory with 27.0% active oxides on the catalyst. The surface area amounted to 1.6 $m^2$/gram. In the acrolein oxidation test at a jacket temperature of 280° C. and a catalyst temperature (maximum) of 305° C. acrolein was converted to the extent of 67.6%, productivity amounted to 16.7 lbs., acrylic acid per cubic foot catalyst per hour at a selectivity of 88.8%.

EXAMPLE 4

(Describes effect of indirect heat exchange)

Catalyst was prepared in a manner described in Example 1. Thermal activation was carried out by placing one liter of the catalyst in a 1.9 liter capacity "bomb" of 15-inch length and externally heated by passing 16000 liters air/hour around the "bomb". Gases generated within the catalyst bed were conducted out of the bomb to a metering system in such a manner that no mixing with the heating air resulted; gases so-generated over the period of the thermal activation amounted to 26-liters of which about 18 liters evolved when the catalyst bed temperatures were in the range of 280°–300° C. and some 5.4 liters additional evolved when the catalyst bed temperatures were in the range of 300°–400° C. The average composition of the evolved gas was 3.7% nitrous oxide, 53.6% nitrogen, 0.4% oxygen, 10.2% water and 32.0% ammonia.

During the heating cycle, over a period of 50 minutes the temperature of the air was raised to 200° C, then over a period of 45 minutes the temperature of the air was raised to 300° C, then over a period of 75 minutes the temperature of the air was raised to 400° C, after which the temperature of the air was held at 400° C for a period of 4.2 hours.

The yield of catalyst was 84% of theory with 27.5% active oxides on the catalyst, the surface area amounted to 2.36 $m^2$/gram. The acrolein oxidation test gave the following results:

| Jacket Temp. °C. | Catalyst temp. °C (Max.) | Conversion % | Productivity lb. acrylic acid per ft.$^3$ cat. per hr. | Selectivity % |
| --- | --- | --- | --- | --- |
| 251 | 294 | 70.3 | 18.9 | 91.3 |
| 265 | 309 | 85.0 | 22.2 | 89.0 |

EXAMPLE 5

(A variation of Example 1 employing a highly dilute solution)

To eight liters of distilled water at 70° C. there were added in succession: 202 grams ammonium paratungstate, 172 grams ammonium metavavadate, 676 grams ammonium paramolybdate, and 24 grams ammonium dichromate and solution was effected in 10 minutes. To the above solution, a solution of 172 grams of cupric nitrate in 600 ml. of distilled water was added with stirring; a dark yellow precipitate formed. The resulting mixture was then stirred rapidly at 88°–90° C. and evaporated to a slurry in about 4.5 hours.

Thereafter, 2080 grams (2 liters) of Norton SA-5218 ¼ inch spheres was added and the mixture was stirred and evaporated on a steam bath to semi-dryness. The final mixture (3335 grams after removing 60 grams of fines) was divided into two parts for use in Examples 6 and 7 below.

EXAMPLE 6

(Thermal activation of ½ of Example 5 catalyst)

One-half of the catalyst prepared in Example 5 was thermally activated in a manner similar to that of Example 2 with a somewhat more rapid heat-up in that in a period of about 30 minutes the air temperature was raised to about 215°–220° C., then over a period of 45 minutes the air temperature was raised to about 400° C. after which the air was held at 400°–410° C. for a period of 5 hours. No ammonia odor was present once the catalyst bed reached about 400° C. The yield of catalyst was 86.9% of theory with 28.0% active oxides on the catalyst.

The catalyst was then used to oxidize acrolein to acrylic acid. At a jacket temperature of 274° C. and a catalyst temperature (maximum) of 305° C., acrolein was converted to the extent of 72.4%, productivity amounted to 16.6 lbs. of acrylic acid per cubic foot of catalyst per hour, and selectivity amounted to 89.5%.

EXAMPLE 7

(Thermal activation of ½ of catalyst of Example 5)

The second half of the catalyst prepared in Example 5 was thermally activated in a manner similar to Example 6, with an even more rapid heat-up in that in a period of 35 minutes the air temperature was raised to 380° ± 20° C, after which the air was held at this temperature for a period of about 5 hours. In addition a quantity of ammonia in the amount of 160 liters per hr. was added to the 16000 liters per hour of air purged through the catalyst bed. It was observed that a thermocouple placed within the catalyst bed but at the edge-center of the tube showed some 40°–60° C. exotherms over the top-center and bottom-center of the bed indicating oxidation of the ammonia was taking place. A mass spectrometric analysis of the effluent gas under these conditions showed 0.32% hydrogen, 0.94% water, 0.01% ammonia and 0.14% nitric oxide, in addition to the usual constituents of air. After a total of about 90 minutes with the temperature of the catalyst being in the range of 380° ± 20° C. ammonia input was decreased to 80 liters per hour whereupon the edge "hot spot" decreased to about 10°–20° C. above the temperature of the remainder of the bed, and the run was continued for an additional 3½ hours. The yield of catalyst was 92.3% of theory with 29.2% of active oxides on the catalyst.

The catalyst was then used to oxidize acrolein to acrylic acid. At a jacket temperature of 272° C. and a catalyst temperature (maximum) of 306° C. acrolein was converted to the extent of 88.1%, productivity amounted to 21.4 lbs. of acrylic acid per cubic foot of catalyst per hour, and selectivity amounted to 92.3%. This result is comparable to those of Example 4 above.

EXAMPLE 8

(Catalyst preparation as in Example 1)

Catalyst was prepared in a manner similar to the procedure of Example 1 except that a quantity of ammonia in the amount of 259 ml (232 grams) was added to the mixture at 40° C., following the addition of the four ammonium salts to the aqueous cupric nitrate solution. The addition of support and evaporation proceeded, as in Example 1, to semi-dryness. The final mixture (3211 grams, after removing 93 grams of fines) was divided into two parts for use in Examples 9 and 10 below.

EXAMPLE 9

(Thermal activation of ½ of catalyst of Example 8)

One-half of the catalyst prepared in Example 8 was thermally activated in a manner similar to that of Example 6, and over a period of 45 minutes the temperature of the air was raised to 300° C, then over a period of 45 minutes the temperature of the air was raised to about 400° C. after which the temperature of the air was held at 400°–410° C. for 5.2 hours. The yield of catalyst was 78.5% of theory with 26.1% of active oxides on the catalyst.

The catalyst was then used to oxidize acrolein to acrylic acid. At a jacket temperature of 293° C. and a catalyst temperature (maximum) of 305° C. acrolein was converted to the extent of 19.6%, productivity amounted to 4.0 lbs. of acrylic acid per cubic foot of catalyst per hour, and selectivity amounted to 76.0%.

EXAMPLE 10

(Thermal activation of ½ of catalyst of Example 8)

The second half of the catalyst prepared in Example 8 was thermally activated in a manner similar to that of Example 4, and over a period of 45 minutes the temperature of the air was raised to 200° C., then over a period of 30 minutes the temperature of the air was raised to 300° C., then over a period of 105 minutes the temperature of the air was raised to about 400° C. after which the temperature of the air was held at about 400° C. for 4.5 hours. The yield of catalyst was 54.8% of theory with 19.8% active oxides on the catalyst.

The catalyst was then used to oxidize acrolein to acrylic acid. At a jacket temperature of 274° C. and a catalyst temperature (maximum) of 305° C., acrolein was converted to the extent of 75.3%, productivity amounted to 19.5 lbs. of acrylic acid per cubic foot of catalyst per hour, and selectivity amounted to 93.2%.

EXAMPLE 11

(Catalyst preparation as in Example 1)

Catalyst prepared as in Example 1 was thermally treated in a manner similar to Example 2 except that a rapid heat up of the air was employed, i.e., 20 minutes to 300° C., then 20 minutes to 400° C, and then about 5 hours at > 400° C. In addition 160 liters of ammonia per hour was added to the air purged through the catalyst bed during the first hour of the thermal treatment, and thereafter the ammonia addition was cut to 80 liters per hour. At the time the ammonia feed was thus reduced the temperatures at the bed edge-center were 472° C. and the temperature of the top-center of the bed was 453° C., whereas the air inlet temperature was 400° C. The "exotherms" were then 10°–20° C. above the gas inlet temperature for the duration of the run (5 hours total at > 400° C). The yield was 97.1% of theory with 30.2% active oxides on the catalyst.

The catalyst was then used to oxidize acrolein to acrylic acid. At a jacket temperature of 274° C. and a catalyst temperature (maximum) of 304° C. acrolein was converted to the extent of 81.5%, productivity amounted to 19.0 lbs. of acrylic acid per cubic foot of catalyst per hour, and selectivity amounted to 90.4%.

EXAMPLE 12

(Indirect thermal activation of catalyst)

Catalyst prepared as in Example 5 was thermally activated as in Example 4. During the thermal activation, over a period of 30 minutes the temperature of the air was raised to 200° C, then over a period of 30 minutes the temperature of the air was raised to 300° C, then over a period of 60 minutes the temperature of the air was raised to 400° C, after which the temperature of the air was held at about 400° C for a period of 5 hours. The yield of catalyst was 90.4% of theory with 28.9% active oxides on the catalyst.

The catalyst was then used to oxidize acrolein to acrylic acid. At a jacket temperature of 242° C and a catalyst temperature (maximum) of 305° C, acrolein was converted to the extent of 91.3%, productivity amounted to 24.6 lbs. of acrylic acid per cubic foot of catalyst per hour, and selectivity amounted to 93.6%.

The support used in the examples was essentially an (~86/14) $Al_2O_3/SiO_2$ material having an apparent porosity of 36–42% and a surface area of <1 m²/gram. About 100% of the pores in the support had a pore diameter of about 20–180.

The pH of the solutions used in each of the examples for the preparation of the catalysts was in the range of 5 ± 3.

The catalysts prepared in Examples 3, 4, 6, 7, 10, 11 and 12 when subjected to X-ray diffraction, are characterized by a relatively well developed reflection corresponding to a lattice spacing of approximately 4 A and a cluster of weaker peaks in the 3 to 4 A interval.

Table I below provides a synopsis of the manner of preparing the various catalysts disclosed in the Examples above, and a listing of the utility of each of such catalysts in terms of the % conversions, productivities and % selectivities achieved, as noted in the examples, when the catalysts were used to oxidize acrolein to acrylic acid.

As disclosed in Table I, "dilution" refers to the volume of water (liters) used per ~1250 grams of soluble compounds used;

"NH₄" refers to whether the ammonia added, as ammonium salts, was "removed" (by the use of direct heat exchange means) from the system prior to the thermal activation step, or was "retained" in the system (by the use of indirect heat exchange means); or whether additional ammonia was "added" to the system, apart from that added as ammonium salts, so as to insure the presence of ammonia during the thermal activation step;

"thermal activation" refers to whether "direct" or "indirect" heat exchange means (as a flow of heated air or nitrogen) was used to thermally activate the catalyst.

The results of the Examples show, in general, that the presence of ammonia during the thermal activation step (at ~350° to 450° C) is needed to provide the most useful catalysts; that the use of indirect heat exchange means facilitates the retention of the ammonia during the heat activation step; and that further improvements in the catalysts are possible when the catalysts are prepared from highly dilute solutions thereof.

TABLE I

| | CATALYST PREPARATION | | | % Active Oxides in Catalyst | CATALYST UTILITY | | |
|---|---|---|---|---|---|---|---|
| Ex. | Dilution | NH₄ | Thermal Activation | | % Conv. | Prod-lbs.acid/ ft³ cat./hr. | % select. |
| 2 | ~1.6 | removed | direct | 26.2 | 40.8 | 9.4 | 77.9 |
| 3 | ~1.6 | removed | direct | 27.0 | 67.6 | 16.7 | 88.8 |
| 4a | ~1.6 | retained | indirect | 27.5 | 70.3 | 18.9 | 91.3 |
| 4b | ~1.6 | retained | indirect | 27.5 | 85.0 | 22.2 | 89.0 |
| 6 | 8.6 | removed | direct | 28.0 | 72.4 | 16.6 | 89.5 |
| 7 | 8.6 | added | direct | 29.2 | 88.1 | 21.4 | 92.3 |
| 9 | ~1.6 | added and removed | direct | 26.1 | 19.6 | 4.0 | 76 |
| 10 | ~1.6 | added and retained | indirect | 19.8 | 75.3 | 19.5 | 93.2 |
| 11 | ~1.6 | added | direct | 30.2 | 81.5 | 19.0 | 90.4 |
| 12 | 8.6 | retained | indirect | 28.9 | 91.3 | 24.6 | 93.6 |

What is claimed is:

1. A process for the production of unsaturated aliphatic carboxylic acid by vapor phase catalytic oxidation of the corresponding unsaturated aliphatic aldehyde with molecular oxygen in the presence of steam in a ratio of about 0.2 to 5 moles of oxygen and about 1 to 25 moles of steam per mole of aldehyde in the reaction mixture, said aldehyde having the structure

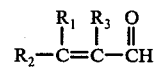

wherein $R_1$ is H or a $C_1$ to $C_6$ alkyl radical, and $R_2$ and $R_3$ are the same or different and are H or $CH_3$, which comprises contacting the reaction mixture, at a temperature of from about 275° to 375° C. and at a pressure of from about 1 to 10 atmospheres, with an oxidation catalyst which has been thermally activated at a temperature of about 350° C. to 450° C. for about 2-24 hours in an atmosphere containing ammonia and which comprises a calcined composition containing the elements Mo, V, W, Cr and Cu in the ratio

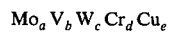

wherein
a is 12,
b is 1 to 6,
c is 1 to 6,
d is 0 to 2, and
e is 1 to 4.

2. A process as in claim 1 in which said unsaturated aliphatic acid is acrylic acid and said unsaturated aliphatic aldehyde is acrolein.

3. A process as in claim 2 in which said oxidation catalyst is supported on an inert support.

4. A process as in claim 3 in which said support is silica, alumina or silica-alumina.

5. A process as in claim 1 in which
a is 12,
b is 4 to 5,
c is 2 to 3,
d is 0.5 to 1,
e is 2 to 3.

6. A process for the production of unsaturated aliphatic carboxylic acid by vapor phase catalytic oxidation of the corresponding unsaturated aliphatic aldehyde with molecular oxygen in the presence of steam in a ratio of about 0.2 to 5 moles of oxygen and about 1 to 25 moles of steam per mole of aldehyde in the reaction mixture, said aldehyde having the structure

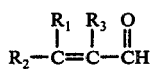

wherein $R_1$ is H or a $C_1$ to $C_6$ alkyl radical, and $R_2$ and $R_3$ are the same or different and are H or $CH_3$, which comprises contacting the reaction mixture, at a temperature of from about 275° to 375° C. and at a pressure of from about 1 to 10 atmospheres, with an oxidation catalyst which has been thermally activated at a temperature of about 350° C. to 450° C. for about 2–24 hours in an atmosphere containing ammonia and which consists essentially of a calcined composition containing the elements Mo, V, W, Cr and Cu in the ratio $$Mo_a V_b W_c Cr_d Cu_e$$

wherein
a is 12,
b is 1 to 6,
c is 1 to 6,
d is 0 to 2, and
e is 1 to 4.

7. A process as in claim 6 in which said unsaturated aliphatic acid is acrylic acid and said unsaturated aliphatic aldehyde is acrolein.

8. A process as in claim 7 in which said oxidation catalyst is supported on an inert support.

9. A process as in claim 8 in which said support is silica, alumina or silica-alumina.

10. A process as in claim 6 in which
a is 12,
b is 4 to 5,
c is 2 to 3,
d is 0.5 to 1,
e is 2 to 3.